US006966903B2

(12) United States Patent
Jonkman et al.

(10) Patent No.: US 6,966,903 B2
(45) Date of Patent: Nov. 22, 2005

(54) INTRAVASCULAR BALLOON OCCLUSION DEVICE AND METHOD FOR USING THE SAME

(75) Inventors: Kenneth R. Jonkman, Grand Rapids, MI (US); Paul F. Rom, Kentwood, MI (US)

(73) Assignee: Medtronic, Inc., Minneapolis, MN (US)

( * ) Notice: Subject to any disclaimer, the term of this patent is extended or adjusted under 35 U.S.C. 154(b) by 138 days.

(21) Appl. No.: 10/470,593

(22) Filed: Mar. 18, 2003

(65) Prior Publication Data

US 2004/0158316 A1   Aug. 12, 2004

Related U.S. Application Data

(60) Continuation of application No. 09/432,624, filed on Nov. 3, 1999, now Pat. No. 6,565,527, which is a division of application No. 08/959,910, filed on Oct. 29, 1997, now abandoned, which is a division of application No. 08/635,415, filed on Apr. 26, 1996, now abandoned.

(51) Int. Cl.[7] ............................................ A61M 31/00
(52) U.S. Cl. ...................................... 604/509; 623/904
(58) Field of Search ....................... 604/96.01, 101.01, 604/101.02, 500, 509; 606/153, 184, 185, 606/170, 167, 191, 194; 623/1.11, 1.13, 904

(56) References Cited

U.S. PATENT DOCUMENTS

| | | | |
|---|---|---|---|
| 4,263,917 A | 4/1981 | Moss | 128/656 |
| 4,627,837 A | 12/1986 | Gonzalo | 604/101 |
| 4,836,204 A | 6/1989 | Landymore et al. | 128/334 |
| 4,909,258 A | 3/1990 | Kuntz et al. | 128/658 |
| 5,301,682 A | 4/1994 | Debbas | 128/737 |
| 5,328,471 A | 7/1994 | Slepian | 604/101 |
| 5,395,330 A | 3/1995 | Marcadis et al. | 604/96 |
| 5,419,765 A | 5/1995 | Weldon et al. | 604/96 |
| 5,437,644 A | 8/1995 | Nobles | 604/165 |
| 5,584,803 A | 12/1996 | Stevens et al. | 604/4 |
| 5,645,566 A | 7/1997 | Brenneman et al. | 606/213 |
| 5,656,013 A | 8/1997 | Yoon | 600/207 |
| 5,662,674 A | 9/1997 | Debbas | 606/192 |
| 5,728,132 A | 3/1998 | Van Tassel et al. | 606/213 |

(Continued)

FOREIGN PATENT DOCUMENTS

EP   0 517 252   12/1992

(Continued)

*Primary Examiner*—Kevin C. Sirmons
(74) *Attorney, Agent, or Firm*—Tom Berry; Jeffrey J. Hohenshell

(57) ABSTRACT

An intravascular balloon occlusion device according to the invention is shown. The device is ideally suited for use in a coronary artery bypass graft procedure. The device includes a body having at least one selectively inflated balloon provided on the distal end thereof. Preferably, the body is a closed end body so that fluid can only flow from the proximal end of the body into the balloon. In use, the distal end of the body and the balloon are inserted into an aperture provided in the aorta. The balloon is inflated and then the device is retracted until the balloon seats against the incision or aperture in the aorta, thereby effectively sealing the aperture from the blood flow through the aorta, but not occluding blood flow through the body of the aorta itself. Next, the graft vessel is telescopically positioned on the occlusion device and mounted to the aorta. Once the vessel is secured thereto, the balloon is deflated and then the occlusion device is retracted from both the aorta and the graft vessel. Finally, the second end of the graft vessel is mounted to the appropriate coronary artery.

32 Claims, 3 Drawing Sheets

U.S. PATENT DOCUMENTS

| | | | |
|---|---|---|---|
| 5,735,290 A | 4/1998 | Sterman et al. | 128/898 |
| 5,924,424 A | 7/1999 | Stevens et al. | 128/898 |
| 6,071,300 A | 6/2000 | Brenneman et al. | 606/213 |
| 6,464,664 B1 * | 10/2002 | Jonkman et al. | 604/96.01 |

FOREIGN PATENT DOCUMENTS

| | | |
|---|---|---|
| EP | 0 655 223 | 5/1995 |

\* cited by examiner

INTRAVASCULAR BALLOON OCCLUSION DEVICE AND METHOD FOR USING THE SAME

This is a continuation of U.S. application Ser. No. 09/432,624, filed Nov. 3, 1999 now U.S. Pat. No. 6,565,527, which is a division of U.S. application Ser. No. 08/959,910, filed Oct. 29, 1997, abandoned, which is a division of U.S. application Ser. No. 08/635,415, filed Apr. 26, 1996, abandoned, all of which are incorporated herein by reference in their entirety.

BACKGROUND OF THE INVENTION

1. Field of the Invention

This invention relates to an intravascular balloon occlusion device, a portion of which is adapted to be positioned inside a vessel during surgical procedures and, more particularly, to an aortic balloon occlusion device wherein the balloon is adapted to seal portions of the aorta while blood flows therethrough.

2. Description of the Related Art

A current trend in coronary bypass surgery is to utilize a minimally invasive surgical procedure. In such a procedure, there is no need to open the chest through a conventional open heart surgical procedure. Rather, multiple access points are created for the receipt of the necessary surgical tools. This procedure has the distinct advantages of mining trauma to the tissue surrounding the heart and chest cavity.

In performing a coronary bypass, one end of a bypass vein is attached to the ascending aorta while the other end of the bypass artery is attached to the coronary artery, downstream from the blockage or occlusion. In attaching one end of the bypass artery to the aorta, it is necessary to create a hole in the aorta, providing an aperture for suturing the end of the bypass artery. The typical procedure is to cross clamp the aorta to stop the blood flow. A problem with this procedure is that it is desirable to continue blood flow through the aorta at all times in order to continue blood flow throughout the body. However, if the surgeon were to punch a hole in the aorta while the blood was flowing therethrough, some blood would flow out the hole, thereby flooding the surgical field with blood and increasing the patient's blood loss during the surgical procedure.

One problem with the prior art coronary artery bypass graft procedures and instruments used therefore is providing means for sealing the aorta so that the hole punches and grafts can be formed therein while continuing the flow of blood through the aorta.

SUMMARY OF THE INVENTION

The intravascular balloon occlusion device according to the invention overcomes the problems of the prior art by providing occlusion means such as a balloon on a body for effectively sealing a portion of the side wall of the aorta from the hollow interior thereof during the anastomosis process. These advantages are all realized while blood continues to flow through the aorta.

The invention comprises an intravascular occlusion device comprising an occlusion device body having a proximal end and a distal end. Preferably, the proximal end is closed so that fluid does not flow from the occlusion device body into a vessel. A connector is provided on the proximal end of the body and a first inflatable member is provided on the exterior surface of the distal end of the body. The inflatable member is adapted for inflation between a retracted state and an expanded state. A first inflation lumen is formed in the body. One end of the lumen is fluidly connected to the first inflatable member. Preferably, the second end of the lumen extends to the connector. The occlusion device according to the invention is adapted to be inserted into an aperture formed in a side wall of a blood vessel when the first inflatable member is in the retracted state. Next, the first inflatable member is expanded so that the inflatable member can be drawn against the interior of the vessel and substantially seal the side wall aperture from the fluid flowing through the vessel.

Preferably, the device includes a second inflatable member provided on the exterior surface of the balloon as a back up to the first member in the event of failure of the first inflatable member. The second inflatable member is independently inflated by fluid passing through a second inflation lumen formed in the body.

In an alternative embodiment, an irrigation aperture is provided in the body of the device proximally of the first and second inflatable members. An irrigation lumen extends to the body from the irrigation aperture to the proximal end of the body, preferably the connector. With this structure, the user can irrigate the area proximally of the first inflation member thereby keeping the surgical field clear.

In an alternative embodiment, a high pressure balloon is provided on the body of the device proximally of the first and second inflation members. Inflation of the high pressure balloon is controlled through a stent inflation lumen extending through the body. The high pressure balloon is used in assisting in the anastomosis process to expand a stent-like anastomosis device which telescopically surrounds the high pressure balloon.

The occlusion device according to the invention can also be adapted for use with a modified vessel punch. Punches are typically used to form an aperture in the side wall of a vessel. In this case, the punch comprises a hollow body having a cutting flange provided at one end thereof and a head member slideably mounted inside the hollow body. The head member is adapted to cooperate with the circular flange and cut a circular aperture in the vessel wall. The hollow body of the punch is dimensioned to simultaneously receive both the head member and the occlusion device. With this structure, the aperture can be formed in the vessel wall with the punch, and then the occlusion device can be inserted into the vessel without withdrawing the punch from the vessel aperture.

In another aspect, the invention relates to a method of performing a coronary artery bypass graft comprising the steps of providing an occlusion device as described above and providing a graft vessel. An incision is formed in the side wall of the aorta, and the distal end of the occlusion device is inserted through the incision a sufficient distance until the first inflatable member, in the retracted, state, is received in the aorta. Next, fluid is supplied to the first inflatable member through the inflation lumen, thereby expanding the inflatable member inside the aorta. The occlusion device is withdrawn from the aorta until the expanded first inflatable member contacts the interior of the sidewall of the aorta and substantially seals the incision from fluid flowing therethrough. The graft vessel is telescopically mounted on the exterior of the occlusion device body and then slid into position adjacent the incision. Next, the vessel is sutured to the aorta or "stented" into place using the high pressure balloon. Finally, the fluid from the first inflatable member is withdrawn causing the inflatable member to assume the retracted state, and then the occlusion device is withdrawn from the aorta and graft vessel.

BRIEF DESCRIPTION OF THE DRAWINGS

The invention will now be described with reference to the drawings in which.

DETAILED DESCRIPTION OF THE PREFERRED EMBODIMENTS

Figure 1:
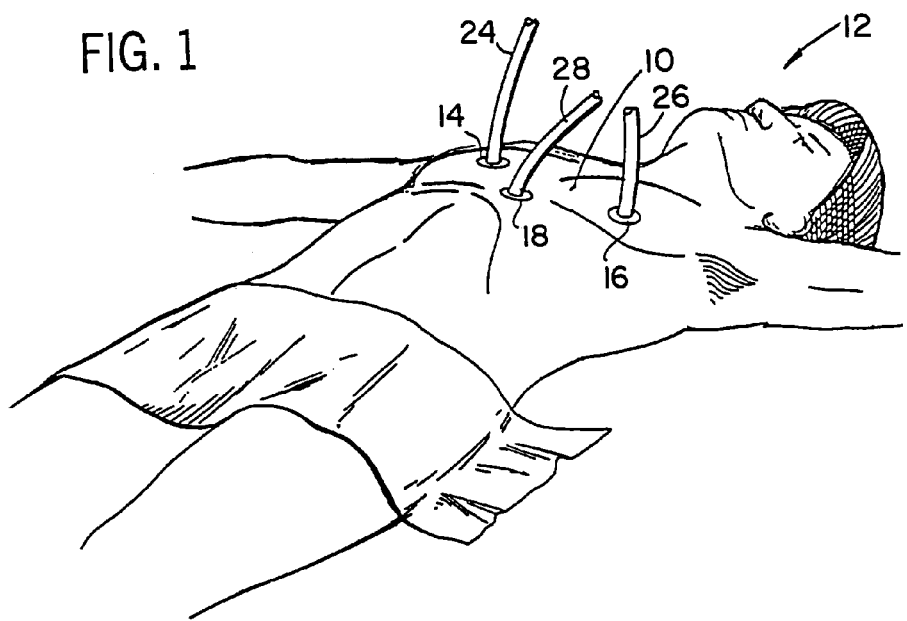
FIG. 1 is a perspective view of a patient during a minimally invasive coronary bypass graft procedure.

In minimally invasive surgical procedures, such as that shown in FIG. 1, multiple small incisions are made in the chest wall for receipt of surgical instruments. For example, two relatively small incisions are made in the chest wall 10 of a patient 12 at different, small interstitial rib positions, while a third incision is made just below the sternum. A first trocar 14 is inserted into the first incision at one of the interstices while a second trocar 16 is inserted into the second incision at another of the interstices. Preferably, the first and second incisions are made on opposite sides of the sternum. A third trocar 18 is inserted into the incision just below the sternum. Each trocar is conventional in nature and has a central aperture (not shown) formed therein. The central aperture is adapted to receive one of a variety of surgical instruments such as an endoscope, electro-cautery pen and the like for performing the minimally invasive surgical procedures. First, second and third conventional surgical instruments are depicted by numerals 24, 26 and 28 in FIG. 1.

Figure 2:
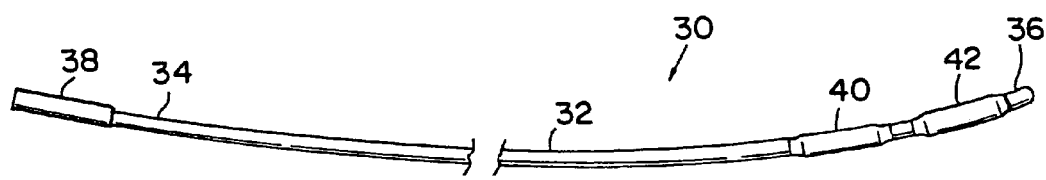
FIG. 2 is a side elevational view of an intravascular balloon occlusion device according to the invention showing the balloons in the deflated state.

Referring now to FIG. 2, an intravascular balloon occlusion device 30 is shown. This device is ideally suited for use in a minimally invasive surgical procedure. However, a person skilled in the art will easily recognize its application in other surgical procedures, such as a conventional open-heart coronary bypass procedure. While the device is described as an aortic balloon assembly, the invention can be utilized in any vessel in which the vessel is dimensioned to receive a combined balloon and pump assembly as described herein.

Figure 4:
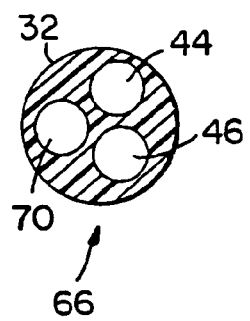
FIG. 4 is a sectional view of the body of the occlusion device taken along lines 4—4 of FIG. 3.
Figure 5:
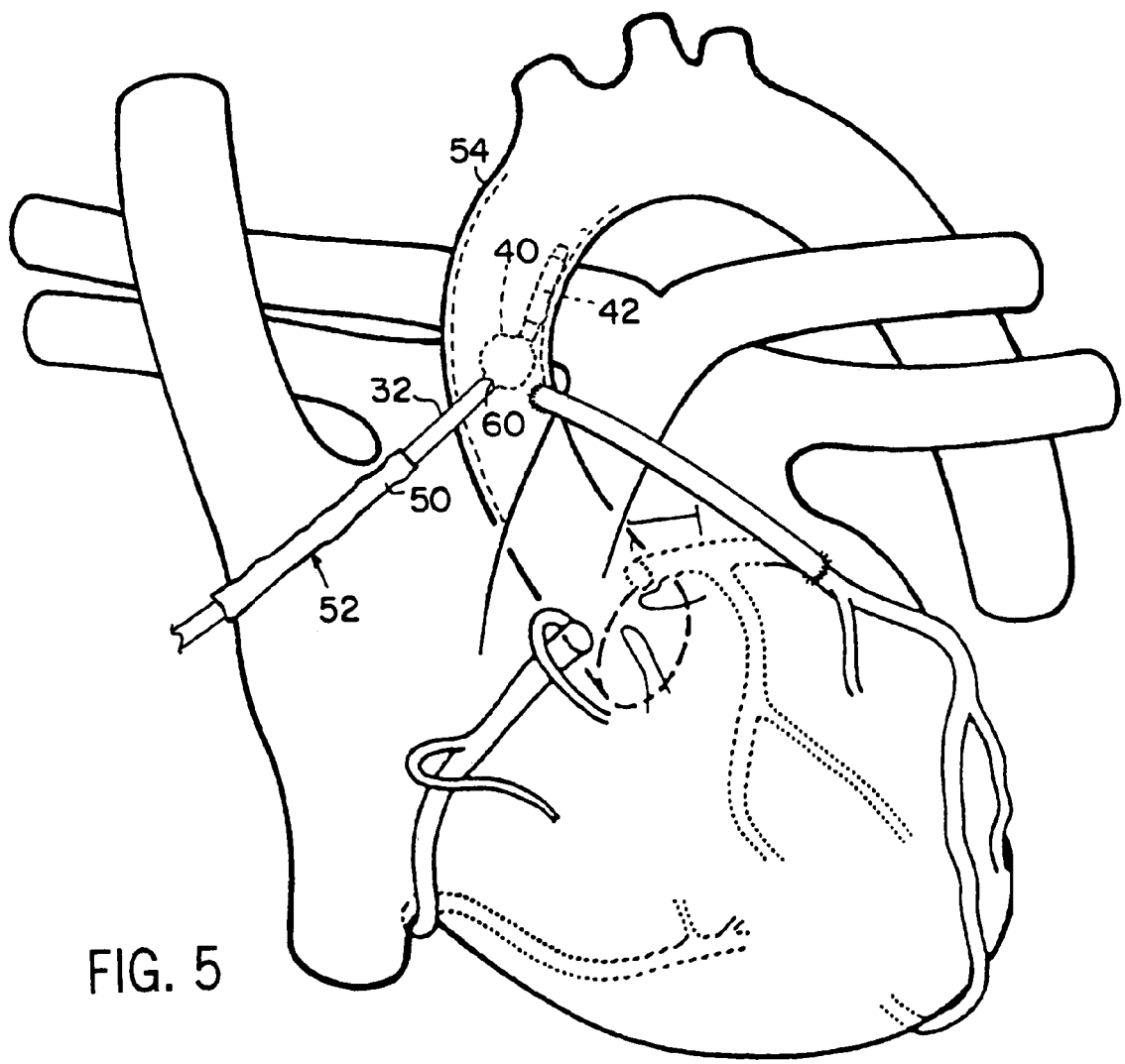
FIG. 5 is a partial, perspective view of a heart and surrounding veins and arteries showing the intravascular balloon occlusion device in use during a coronary artery bypass graft procedure.

The intravascular balloon occlusion device 30 according to the invention comprises a body 32 having a proximal end 34 and a distal end 36. Preferably, a low profile connector 38 is provided on the proximal end and a pair of expandable members or balloons 40, 42 are provided adjacent the distal end 36. Each balloon is adapted for expansion between a deflated state as seen in FIG. 2 and an expanded state as seen in FIG. 4. A first lumen 44 (FIG. 4) extends from the first balloon 40 to the proximal end 34. Similarly, a second lumen 46 (FIG. 4) extends from the second balloon 42 to the proximal end 34. Each balloon 40, 42 is selectively inflated by providing fluid under pressure through the appropriate lumen to the balloon. Preferably, the connector 38 is adapted to be mounted to a suitable source for supplying pressurized fluid to the balloons.

The intravascular balloon occlusion device 30 according to the invention is ideally suited for use in a coronary artery graft procedure wherein a first end 50 of a harvested graft vessel 52 is attached to the aorta 54 and the second end of the graft vessel 52 is attached to the occluded or blocked coronary artery, downstream from the blockage or occlusion. While this is the preferred application for the invention, those skilled in the art will appreciate other applications for the invention.

In practice, the harvested graft vessel 52 is telescopically received on to the exterior of the catheter body 32. Once the graft is positioned telescopically, an incision 60 is formed in the side wall of the aorta 54. Next, the distal end 36 of the device 30 is inserted through the incision 60 until at least both balloons 40, 42 are received therein. The proximal balloon 40 is then inflated by pressurized fluid supplied through the lumen 44, and the inflation device is retracted until the balloon 40 is drawn up against the interior surface 62 of the aorta 54. The inflated balloon will occlude the incision 60 from the pressurized blood flow through the aorta thereby minimizing loss of blood through the incision 60 during the anastomosis process for the graft vessel 52. Once the proximal balloon 40 is properly positioned to seal the incision, the graft vessel 52 is slid along the length of the catheter body 32 until the first end 50 of the graft vessel 52 is positioned for attachment to the aorta 54. When the vessel 52 has been sutured to the aorta 54, the proximal balloon 40 is deflated by withdrawing all fluid contained therein through the first lumen 44. Finally, the occlusion device 30 is withdrawn from the aorta and the graft vessel 52. As the device is being withdrawn, the graft vessel 52 can be clamped with a conventional surgical clamp to prevent the blood flowing through the aorta from passing through the graft vessel. Finally, the second end of the graft vessel is surgically attached to the blocked or occluded coronary artery. Once this is completed, then the clamp on the graft vessel can be removed, thereby completing the bypass procedure.

The preferred embodiment of the invention includes two balloons, the distal balloon 36 being a backup balloon in the event that the proximal balloon 40 is ruptured or fails during the procedure. In the event that the proximal balloon 40 fails, this balloon 40 would be drained of all fluid and returned to the deflated state. Next, the distal balloon 42 would be inflated and then the catheter 30 would be withdrawn from the aorta until the distal balloon 42 contacted the incision and effectively sealed the incision from the blood flowing through the aorta 54. While the preferred embodiment includes two balloons, an occlusion device having only one balloon provided thereon is within the scope of the invention. Alternatively, more than two balloons could be formed thereon for multiple backups.

Figure 3:
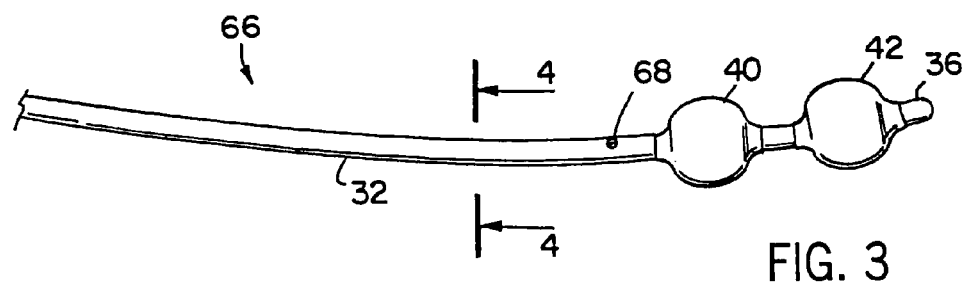
FIG. 3 is a side elevational view of a second embodiment of an intravascular balloon occlusion device according to the invention showing the balloons in the deflated state.

FIG. 3 shows a second embodiment of the occlusion device 66 according to the invention. The primary distinction between this embodiment and the first embodiment is the incorporation of at least one irrigation aperture 68 provided adjacent the proximal balloon 40. The irrigation aperture 68 is provided at the end of an irrigation lumen 70

(FIG. 4) which extends through the body of the occlusion device 30 to the connector 38 where it is connected to a suitable source. The irrigation aperture 68 is preferably positioned immediately adjacent the incision 60 in the aorta 54 when the occlusion device 30 is in position to seal the incision 60. With this structure, the surgical field immediately adjacent the anastomosis site can be irrigated, thereby keeping the field clear for completion of the procedure. The sectional view of the body of the occlusion device as seen in FIG. 4 is substantially identical to that in the first embodiment except that the second embodiment includes an additional lumen, the irrigation lumen 70.

Figure 8:
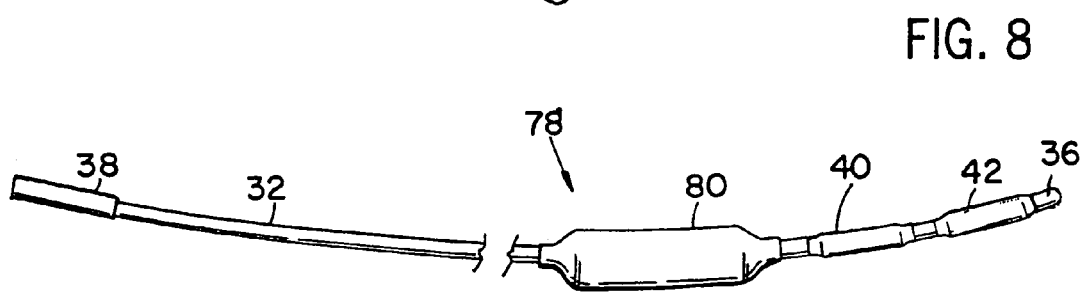
FIG. 8 is a partial side elevational view of a third embodiment of an intravascular balloon occlusion device according to the invention.

Still another embodiment of the occlusion device is seen in FIG. 8. In this embodiment of the occlusion device 78, a high pressure balloon 80 is provided on the body 32, proximally of the proximal occlusion balloon 40. The high pressure balloon is fluidly connected to the connector 38 by a lumen extending from the high pressure balloon 80 to the connector. The cross section of the body of the third embodiment 78 is substantially identical to that seen in FIG. 4, except that the third lumen is used for inflation of the high pressure balloon rather than irrigation, as described above with respect to FIG. 4. The high pressure balloon 80 is adapted to selectively expand a known expandable stent which is telescopically received on the outside of the balloon 80 but inside the graft vessel. Examples of stents suitable for use according to the invention include those seen in U.S. Pat. Nos. 4,886,062 to Wiktor, 5,133,732 to Wiktor, and 4,733,665 to Palmaz, each of these patents being incorporated herein by reference.

Figure 6:
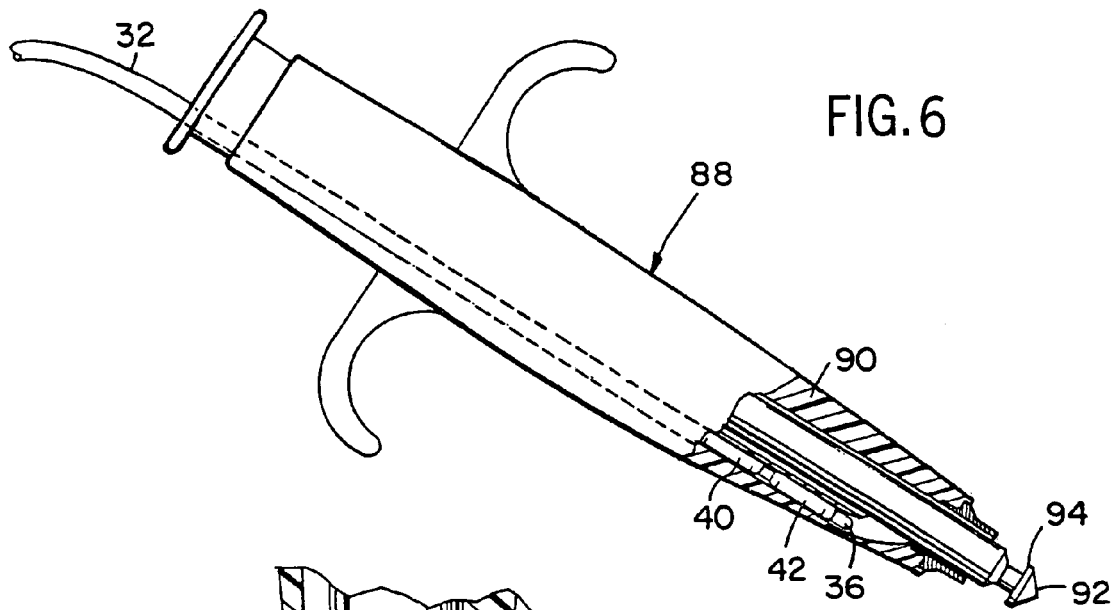
FIG. 6 is a side elevational view of an aortic punch in combination with an intravascular balloon occlusion device according to the invention.
Figure 7:
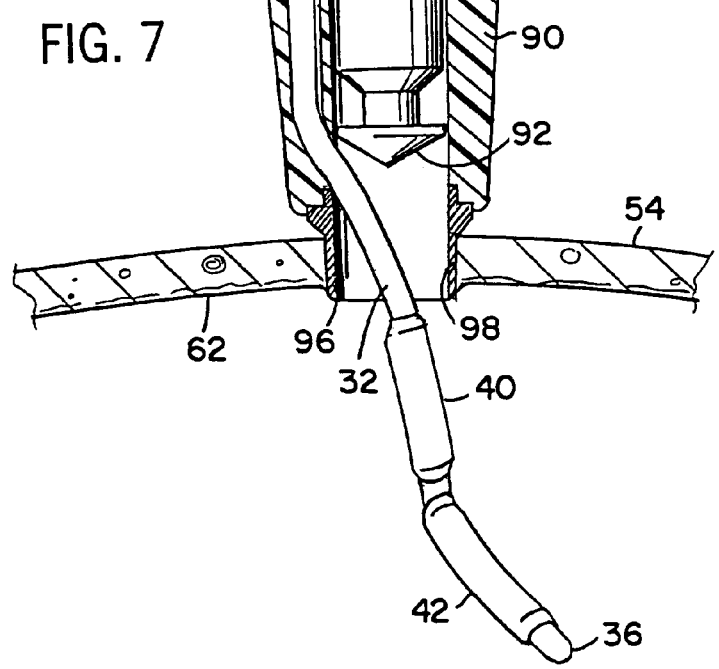
FIG. 7 is a partial sectional view of the aortic punch and intravascular balloon occlusion device of FIG. 6 showing the catheter and punch in position during a graft procedure.

FIGS. 6 and 7 show an alternative means for inserting the occlusion device 30 according to the invention into the incision of the aorta In this embodiment, the occlusion device 30 is integrated with an aortic punch 88. The punch 88 comprises a tubular body 90 which telescopically receives a spring loaded head 92 therein. The head has a sharpened edge 94 which cooperates with a circular flange 96 provided on the tubular body 90, the flange 96 having a sharpened edge which cooperates with the head 92 to cut a circular shaped aperture in the aorta. The first end 50 of the graft vessel 52 is attached to the aorta at the circular aperture formed by the punch 88. A punch, as described above, is well known in the art. In this invention, the conventional structure of the punch is modified to incorporate the balloon occlusion device 30 according to the invention. As seen in FIG. 6, the occlusion device 30 is telesopically received inside the body 90 of the punch 88.

In practice, the head 92 is extended from the body and inserted into an incision 60 formed in the aorta. Next, the flange 96 is positioned immediately adjacent the aorta and then the head 92 is retracted back into the body 90, the retraction of the head 92 past the flange 96 cuts the circular aperture. Keeping the flange 96 in place against the aperture 98, the head 92 is retracted a sufficient distance into the body 90 to permit the distal end 36 of the occlusion device 30 to pass through the circular flange 96 into the aperture 98 and the interior of the aorta 54. Once the device 30 has been inserted a sufficient distance so that both the proximal and distal balloons 40, 42 are received in the interior of the aorta, the proximal balloon 40 is inflated as described previously, thereby sealing the aperture 98 in the aorta 54. Next, the aorta punch 88 is slidably removed from the aperture 98 and the occlusion device 30 and the anastomosis process proceeds as described above. In this embodiment, the graft vessel 52 preferably is not mounted on the occlusion device until after the aortic punch 88 has been removed therefrom. This prevents potential damage to the vessel during the punching operation.

The occlusion device according to the invention provides several significant advantages over the prior art. Namely, the occlusion device provides a means to seal the incisions and apertures formed in the aorta during a coronary artery bypass graft so that there is no need to clamp the aorta during the anastomosis process. Therefore, blood can continue to flow through the body. In addition, other inherent problems experienced in clamping the aorta, such as dislodging plaque on the inside of the aorta is eliminated. This process is ideally suited for patients having extensive plaque on the interior of the aorta which would prevent clamping of the aorta during the bypass graft procedure. Clamping of the aorta has always been a problem in performing a coronary artery bypass graft The occlusion device according to the invention eliminates the need for this step and therefore is a significant improvement over the prior art.

Reasonable variation and modification are possible within the spirit of the foregoing specification and drawings without departing from the scope of the invention.

What is claimed is:

1. A method of securing a graft to a side wall of an aorta comprising:
   providing an aperture-forming device having a passageway therethrough;
   providing an occlusion device comprising an elongated body and an occlusion member at a distal end thereof, the occlusion device sized to permit the elongated body of the occlusion device to be slideably received within passageway of the aperture-forming device;
   engaging a portion of the side wall of the aorta with the aperture-forming device so as to form an aperture in the side wall of the aorta while blood continues to flow through the aorta;
   advancing the elongated body of the occlusion device through the passageway of the aperture-forming device while maintaining the aperture-forming device in sealing engagement with the portion of the aorta, the elongated body of the occlusion device advanced until the distal end of the occlusion device extends into the aperture;
   occluding the aperture with the occlusion member;
   withdrawing the aperture forming device while the occlusion device occludes the aperture;
   mounting a graft on the occlusion device body;
   securing the first end of the graft to the side wall of the aorta about the aperture;
   removing the occluding member; and
   withdrawing the occlusion device from the graft.

2. The method according to claim 1 further comprising clamping closed the graft to prevent the flow of fluid therethrough.

3. The method according to claim 2 wherein the graft is clamped prior to fully withdrawing the occlusion device therefrom.

4. The method according to claim 1 further comprising securing a second end of the graft to a coronary artery.

5. The method according to claim 1 wherein the graft vessel is mounted on the occlusion device body by telescopically receiving the graft on the occlusion device body.

6. The method according to claim 1 wherein the aperture-forming device is a vessel punch.

7. The method according to claim 1 wherein the occlusion member is a balloon that occludes the aperture.

8. The method according to claim 7 wherein the balloon is inflated to occlude the aperture.

9. The method according to claim 1 wherein the first end of the graft is secured to the side wall of the aorta by suturing.

10. The method according to claim 1 wherein the first end of the graft is secured to the side wall of the aorta by an expansible stent-like anastomosis device.

11. The method according to claim 1 wherein occluding the aperture with the occlusion member occludes the aperture without stopping blood flow within the aorta.

12. The method according to claim 1 wherein the occlusion device includes a second occlusion member and the second occlusion member occludes the aperture.

13. The method according to claim 1 wherein the occlusion device includes a stent expansion member.

14. A method of forming an aperture in a side wall of an aorta comprising:
providing an aperture-forming device;
providing an occlusion device comprising an elongated body and an occlusion member at a distal end thereof;
engaging a portion of the side wall of the aorta with the aperture-forming device so as to form an aperture in the side wall of the aorta while blood continues to flow through the aorta;
advancing a portion of the elongated body of the occlusion device into the aperture while maintaining the aperture-forming device in sealing engagement with the portion of the aorta, the elongated body of the occlusion device advanced until the distal end of the occlusion device extends into the aperture;
occluding the aperture with the occlusion member; and
withdrawing the aperture forming device while the occlusion device occludes the aperture.

15. The method according to claim 14 wherein the aperture-forming device is a vessel punch.

16. The method according to claim 14 wherein the occlusion member is a balloon.

17. The method according to claim 16 wherein the balloon is inflated to occlude the aperture.

18. The method according to claim 14 wherein occluding the aperture with the occlusion member occludes the aperture without stopping blood flow within the aorta.

19. The method according to claim 14 wherein the occlusion device includes a second occlusion member and the second occlusion member occludes the aperture.

20. The method according to claim 14 wherein the occlusion device is slideably received within the aperture-forming device as the occlusion device is advanced.

21. A method of performing a bypass grafting procedure comprising:
providing an aperture-forming device;
providing an occlusion device comprising an elongated body and an occlusion member at a distal end thereof;
engaging a portion of a side wall of an aorta with the aperture-forming device so as to form an aperture in the side wall of the aorta while blood continues to flow through the aorta;
advancing a portion of the elongated body of the occlusion device into the aperture while maintaining the aperture-forming device in sealing engagement with the portion of the aorta, the elongated body of the occlusion device advanced until the distal end of the occlusion device extends into the aperture;
occluding the aperture with the occlusion member;
withdrawing the aperture-forming device while the occlusion device occludes the aperture;
mounting a graft vessel on the occlusion device body;
securing a first end of the graft vessel to the side wall of the aorta about the aperture;
removing the occluding member;
withdrawing the occlusion device from the graft vessel; and
securing a second end of the graft vessel to a coronary artery.

22. The method according to claim 21 further comprising clamping closed the graft vessel after withdrawing the occlusion device to prevent the flow of fluid therethrough.

23. The method according to claim 21 wherein the graft vessel is mounted on the occlusion device body by telescopically receiving the graft vessel on the occlusion device body.

24. The method according to claim 21 wherein the aperture-forming device is a vessel punch.

25. The method according to claim 21 wherein the occlusion member is a balloon that occludes the aperture.

26. The method according to claim 25 wherein the balloon is inflated to occlude the aperture.

27. The method according to claim 21 wherein the first end of the graft vessel is secured to the side wall of the aorta by suturing.

28. The method according to claim 21 wherein the first end of the graft vessel is secured to the side wall of the aorta by an expansible stent-like anastomosis device.

29. The method according to claim 28 wherein the occlusion device includes a stent expansion member.

30. The method according to claim 21 wherein occluding the aperture with the occlusion member occludes the aperture without stopping blood flow within the aorta.

31. The method according to claim 21 wherein the occlusion device includes a second occlusion member and the second occlusion member occludes the aperture.

32. The method according to claim 21 wherein the occlusion device is slideably received within the aperture-forming device as the occlusion device is advanced.

* * * * *